United States Patent [19]
Pagan

[11] Patent Number: 6,152,136
[45] Date of Patent: Nov. 28, 2000

[54] CUFFED TUBE ASSEMBLIES

[75] Inventor: Eric Pagan, Hythe, United Kingdom

[73] Assignee: Smiths Industries Public Limited Company, London, United Kingdom

[21] Appl. No.: 09/076,868

[22] Filed: May 13, 1998

[30] Foreign Application Priority Data

May 22, 1997 [GB] United Kingdom .................. 9710645

[51] Int. Cl.[7] .................................. A61M 16/00
[52] U.S. Cl. ................................ 128/207.15; 128/207.14
[58] Field of Search .................. 128/207.15, 207.14, 128/200.26; 604/282, 283, 96, 103

[56] References Cited

U.S. PATENT DOCUMENTS

| | | | |
|---|---|---|---|
| 3,659,611 | 5/1972 | Miller | 128/207.15 |
| 5,282,464 | 2/1994 | Brain | 128/207.15 |
| 5,305,743 | 4/1994 | Brain | 128/207.15 |
| 5,355,879 | 10/1994 | Brain | 128/207.15 |
| 5,584,290 | 12/1996 | Brain | 128/207.15 |
| 5,682,880 | 11/1997 | Brain | 128/207.15 |
| 5,791,341 | 8/1998 | Bullard | 128/207.15 |

FOREIGN PATENT DOCUMENTS

0712638A1  5/1996  European Pat. Off. .

*Primary Examiner*—John G. Weiss
*Assistant Examiner*—V. Srivastava
*Attorney, Agent, or Firm*—Pollock, Vande Sande & Amernick

[57] ABSTRACT

An endotracheal tube has an inflatable cuff at its patient end enclosing a plate of generally triangular shape projecting forwardly of the patient end of the tube. When deflated, the cuff conforms to the external shape of the plate.

12 Claims, 3 Drawing Sheets

CUFFED TUBE ASSEMBLIES

BACKGROUND OF THE INVENTION

This invention relates to cuffed tubes assemblies.

Various cuffed tubes have an inflatable cuff at their patient end that is deflated for introduction to a body cavity. In some tubes, such as endotracheal tubes, the deflated cuff preferably presents as low a profile as possible. In other tube assemblies, such as laryngeal or pharyngeal mask airways, the cuff preferably has a particular shape when deflated that helps locate the assembly correctly. In such assemblies, the cuff is usually attached to one side of a plate, or the like, of the desired shape. However, because the desired shape of the cuff when inflated is different from that when deflated, this can be difficult to arrange.

SUMMARY OF THE INVENTION

It is an object of the present invention to provide an improved cuffed tube assembly.

According to the present invention there is provided a cuffed tube assembly including a tubular member and a cuff member, the assembly including a plate member projecting outwardly of the tubular member towards its patient end, and the cuff member surrounding the plate member and substantially conforming to the external shape of the plate member when deflated.

The cuff member may be inflatable beyond the patient end of the tubular member, the plate member projecting beyond the patient end of the tubular member. The plate member may be of generally triangular shape and may be inclined away from the axis of the tubular member where it projects beyond the patient end of the tubular member. Alternatively, the tubular member may open through at least one aperture in its wall, the cuff member having a side opening through which the aperture in the tubular member opens. The patient end of the tubular member may project beyond the patient end of the cuff member. The plate member may comprise two wings extending longitudinally on opposite sides of the tubular member in the region of the aperture. The wings may be formed on a component a part of which is inserted within the patient end of the tubular member, which preferably has an inclined surface directed towards the aperture.

Three different forms of cuffed tube assembly according to the present invention, will now be described, by way of example, with reference to the accompanying drawings.

DETAILED DESCRIPTION OF THE PREFERRED EMBODIMENTS

Figure 1:
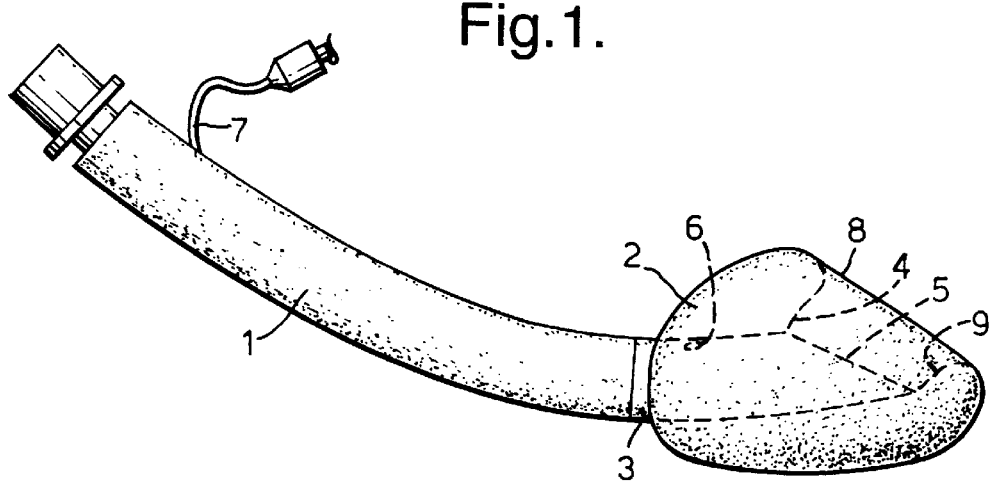
FIG. 1 is a side elevation view of a pharyngeal mask assembly.
Figure 3:
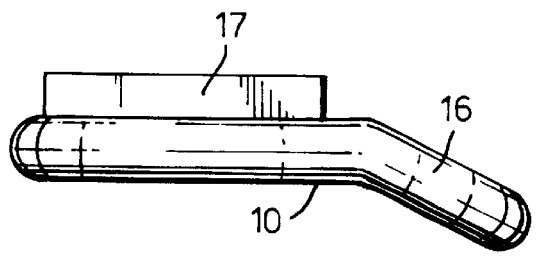
FIG. 3 is a side elevation view of a part of the assembly.
Figure 2:
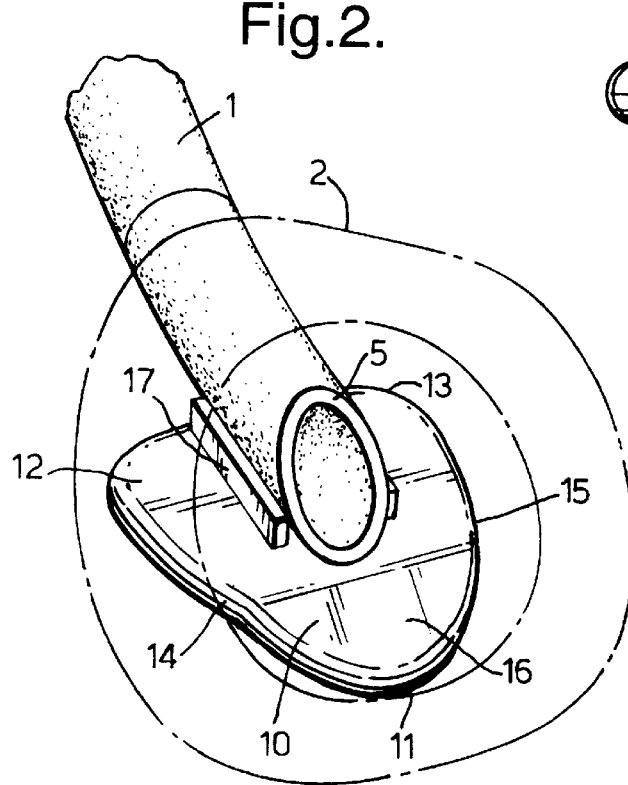
FIG. 2 is a perspective view of the patient end of the assembly of FIG. 1.

With reference first to FIGS. 1 to 3, there is shown a pharyngeal mask assembly having a curved tube 1 with an inflatable cuff 2 at its patient end. The rear end 3 of the cuff 2 is attached to the outside of the tube, the forward end 4 being attached to the forward, bevelled end 5 of the tube. An inflation aperture 6 on the outside of the tube 1 opens within the cuff 2 and communicates with an inflation line 7 via a lumen extending within the wall of the tube. When inflated, as shown, the cuff 2 expands forwardly beyond the forward end of the tube and forms an angled end face 8 with a central opening 9 into the tube, the end face being arranged to seal with tissue around the patient's laryngeal opening. As so far described, the tube is conventional and may be similar to that described in EP-A-712638. The present assembly, however, differs from previous assemblies in that a plastics plate member 10 projects radially outwardly from the tube 1, within the cuff 2. The plate member 10 is of approximately triangular shape with rounded corners 11 to 13 and with two sides 14 and 15 curved slightly outwardly. The plate 10 is attached to the longer side of the tube 1, with the bevelled tip of the tube being set back from the forward apex 11 of the plate 10 by a distance about one third the length of the plate. That part 16 of the plate 10 projecting forwardly beyond the end of the tube 1 is inclined down away from the axis of the tube by about 30° (FIG. 3). The plate 10 has two, parallel low walls 17 projecting from its upper surface rearwardly of the forward part 16, which serve to locate the tube 1 centrally of the plate, so that the sides of the plate project outwardly as two lateral wings.

The cuff 2 is attached to the tube 1 at one end 3 to the rear of the plate 10. The other end 4 of the cuff is attached to the bevelled end surface 5 of the tube 1, so that it encloses the plate 10 and is not attached to it. When the cuff 2 is inflated by air supplied to the inflation line 7, the cuff expands to the shape shown, beyond the boundaries of the plate 10. For insertion and removal of the assembly from the patient, the cuff 2 is deflated by sucking air from the inflation line 7, which has the effect of drawing the wall of the cuff down onto the outside of the tube and onto the upper and lower surfaces of the plate 10. The shape of the plate 10 is chosen so that it helps locate the forward end of the tube 1 in the correct position prior to inflation of the cuff 2 and maintains the deflated cuff in the correct position to ensure that it inflates correctly to the desired shape.

Figure 4:
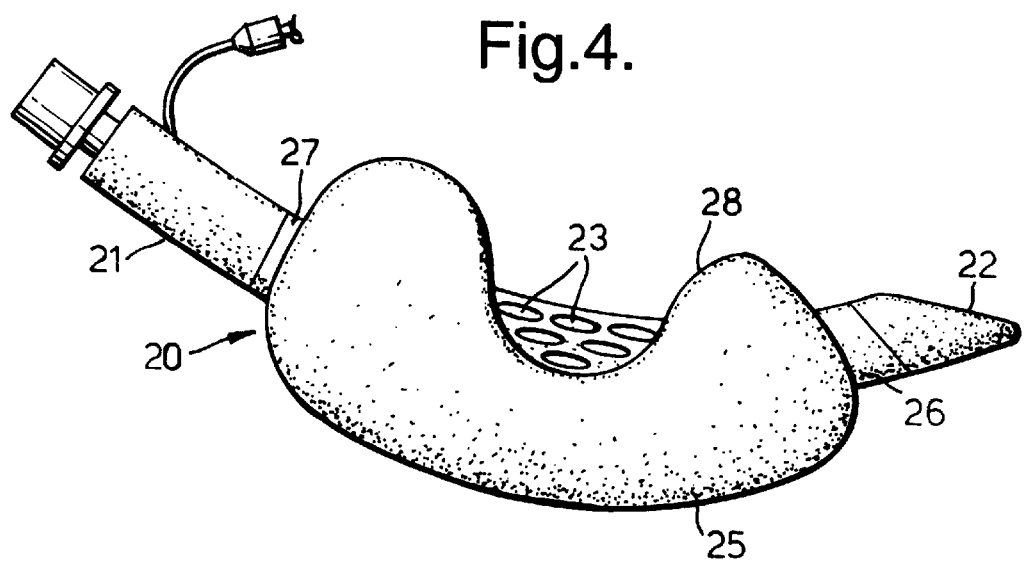
FIG. 4 is a side elevation view of an alternative pharyngeal mask assembly.
Figure 5:
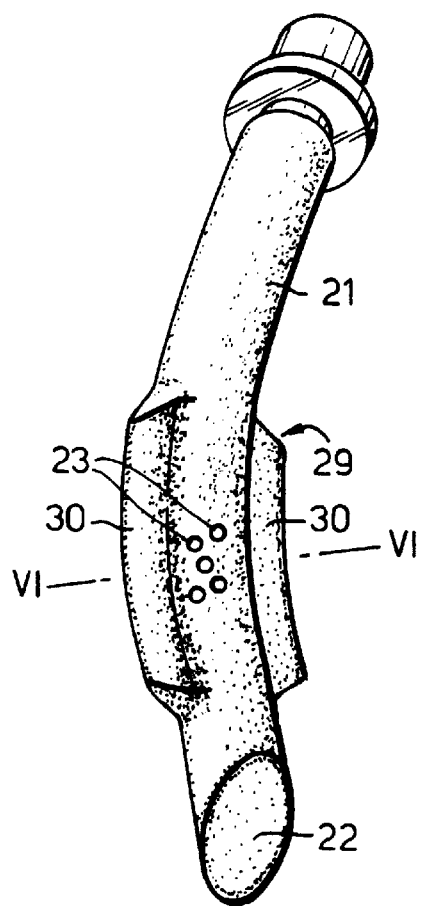
FIG. 5 is a perspective view of the assembly of FIG. 4 without a cuff.
Figure 6:
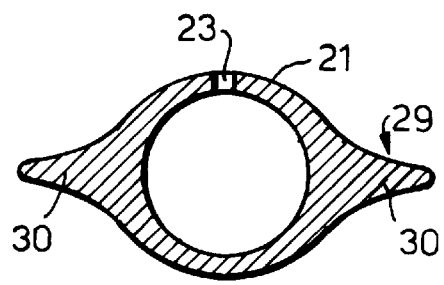
FIG. 6 is a lateral cross section along the line VI—VI of FIG. 5.

With reference now to FIGS. 4 to 6, there is shown an alternative pharyngeal mask assembly 20 having a tube 21, which is closed at its patient end 22 and opens through a number of holes 23 in its side wall spaced a short distance rearwardly of the patient end. The mask assembly 20 has a cuff 25 of generally tubular shape. The forward end 26 of the cuff 25 is attached to the outside of the tube 21 at a location forwardly of the holes 23, the rear end 27 being attached to the tube rearwardly of the holes. The cuff 25 has a side opening 28 the edge of which is also attached to the outside of the tube 21 around the region of the holes 23, so that the holes are exposed externally through the side opening of the cuff. As so far described, this assembly is conventional, such as described in EP-A-712638. The present invention assembly differs from previous assemblies in that the tube 21 has a plate member 29 projecting radially outwardly at the patient end of the tube on opposite sides of the region with the holes 23. The plate 29 takes the form of two narrow wings 30 with tapered ends extending longitudinally and projecting radially outwardly. The plate 29 may be formed in various ways. For example, it could be formed as a separate component or components and subsequently attached to the tube. Alternatively, it could be heat formed from the wall of the tube. Another way of forming the plate would be to extrude the tube with two laterally-projecting wings, so that they extend along the entire length of the tube, and then cut away parts of the wings to leave the desired shape.

In use, the assembly shown in FIGS. 4 to 6 is inserted with the cuff 25 deflated so that the patient end 22 of the tube is located in the lower pharynx, behind the laryngeal opening, and the opening 28 in the cuff is located at the laryngeal inlet. The cuff 25 is then inflated to seal in the pharyngeal region.

Figure 7:
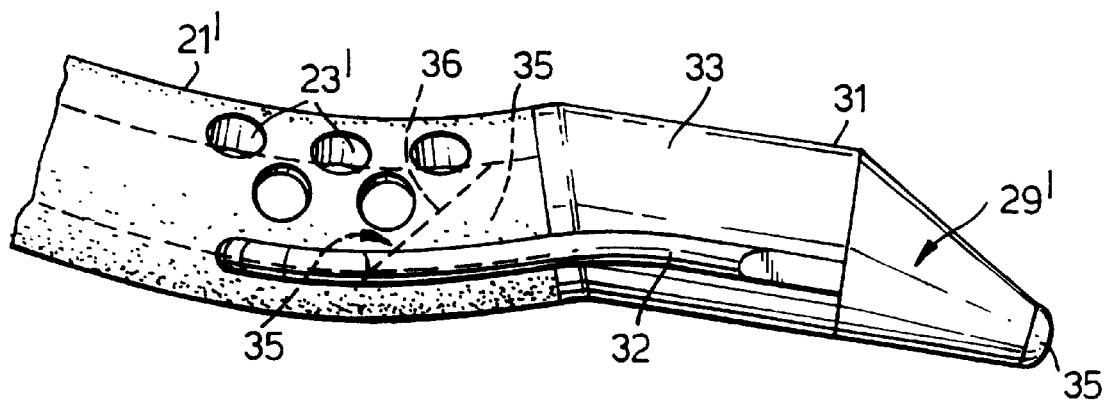
FIG. 7 is a side elevation view of another alternative assembly without a cuff.
Figure 8:
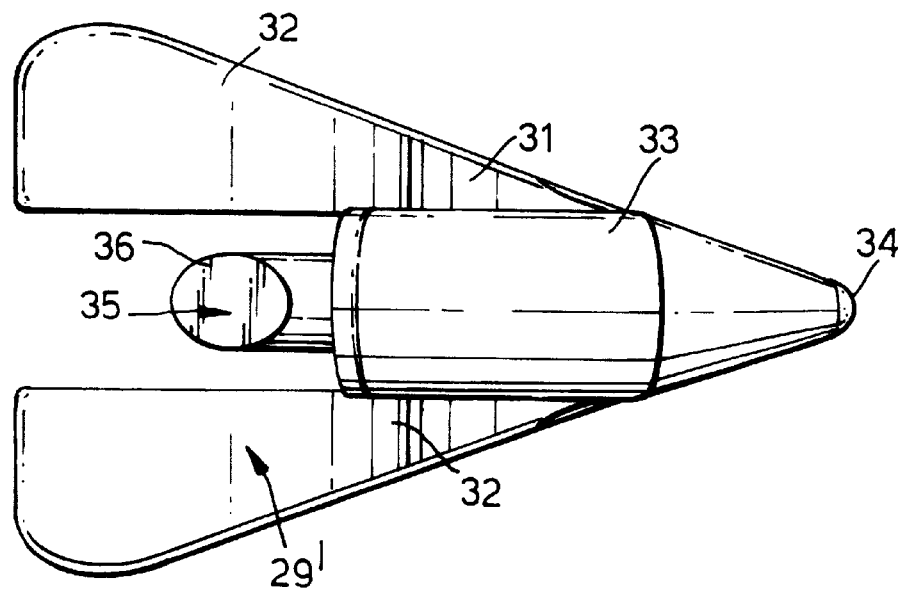
FIG. 8 is a plan view of a part of the alternative assembly of FIG. 7.

FIGS. 7 and 8 illustrate an alternative way of forming the assembly shown in FIG. 4. In this arrangement, the plate 29' is formed on a separate butterfly-shape component 31 shown in FIG. 8. The plate 29' is provided by two wing members 32 of triangular shape extending rearwardly from a nose portion 33. The nose portion 33 has a tapered, rounded tip 34 and a rearwardly-extending spigot 35. The nose portion 33 is inclined down at an angle of about 20° from the axis of the spigot 35. The shape of the spigot 35 is such that it forms a push fit inside the forward end of the tube 21' and has a profiled upper surface to divert a suction catheter (not shown) inserted along the assembly upwardly so that it passes out through the holes 23'. This assembly has the advantage that the spigot 35 reduces deadspace at the patient end of the tube 21'.

What is claimed is:

1. A cuffed tube assembly comprising: a tubular member, said tubular member having a patient end and a machine end; a plate member, said plate member projecting outwardly of said tubular member towards said patient end of said tubular member, and a hollow cuff member, said hollow cuff member enclosing an inflatable volume, said plate member projecting internally of said cuff member within said inflatable volume and said cuff member substantially conforming to an external shape of said plate member when said cuff member is deflated about said plate member.

2. An assembly according to claim 1, wherein said cuff member is inflatable beyond said patient end of said tubular member, and wherein said plate member projects beyond said patient end of said tubular member.

3. An assembly according to claim 2, wherein said plate member is of generally triangular shape.

4. An assembly according to claim 2, wherein said plate member is inclined away from the axis of said tubular member where said plate member projects beyond said patient end of said tubular member.

5. An assembly according to claim 1, wherein said tubular member has at least one aperture in its wall, and wherein said cuff member has a side opening, said aperture in said tubular member opening through said side opening in said cuff member.

6. An assembly according to claim 5, wherein said patient end of said tubular member projects beyond a patient end of said cuff member.

7. An assembly according to claim 5, wherein said plate member comprises two wings extending longitudinally on opposite sides of said tubular member in a region of said aperture.

8. An assembly according to claim 7, wherein said wings are formed on a component, and wherein said component has a part inserted within said patient end of said tubular member.

9. An assembly according to claim 8, wherein said part of said component inserted in said tubular member has an inclined surface directed towards said aperture.

10. A cuffed pharyngeal mask comprising: a tubular member, said tubular member having a patient end and a machine end; a plate member of generally triangular shape, said plate member projecting outwardly of the tubular member towards said patient end of said tubular member and projecting beyond and away from an axis of said tubular member at said patient end; and an inflatable hollow cuff member, said hollow cuff member enclosing an inflatable volume, said cuff member being attached at opposite ends to said tubular member so that said plate member projects inside said cuff member within said inflatable volume, said cuff member substantially conforming to an external shape of said plate member when deflated about said plate member.

11. A cuffed pharyngeal mask assembly comprising: a tubular member, said tubular member having a patient end, a machine end and at least one aperture in a wall of said tubular member; two longitudinally-extending wing members projecting outwardly of said tubular member on opposite sides in a region of said aperture; and an inflatable hollow cuff member, said hollow cuff member enclosing an inflatable volume, said cuff member being attached at opposite ends to said tubular member so that said wing members extend internally of said cuff member within said inflatable volume, said cuff member having a side opening through which said aperture opens, and said cuff member substantially conforming to an external shape of said wing members when deflated about said wing members.

12. A cuffed pharyngeal mask assembly comprising: a tubular member, said tubular member having a patient end, a machine end and at least one aperture in a wall of said tubular member; a butterfly-shape insert, said insert having a spigot inserted in said patient end, a nose projecting from said patient end and two longitudinally-extending wing members projecting outwardly; and an inflatable hollow cuff member, said hollow cuff member enclosing an inflatable volume, said cuff member being attached at opposite ends to said tubular member so that said wing members extend inside said cuff member within said inflatable volume, said cuff member having a side opening through which said aperture opens, and said cuff member substantially conforming to an external shape of said wing members when deflated about said wing members.

* * * * *